US011337610B2

(12) United States Patent
Patil et al.

(10) Patent No.: US 11,337,610 B2
(45) Date of Patent: May 24, 2022

(54) TEMPERATURE MEASUREMENT IN THERMAL THERAPY

(71) Applicants: Siemens Healthcare GmbH, Erlangen (DE); University of Utah Research Foundation, Salt Lake City, UT (US)

(72) Inventors: Sunil Goraksha Patil, Ellicott City, MD (US); Henrik Odeen, Salt Lake City, UT (US); Bhat Himanshu, Newton, MA (US); John Roberts, Salt Lake City, UT (US); Dennis L. Parker, Centerville, UT (US)

(73) Assignees: Siemens Healthcare GmbH, Erlangen (DE); University of Utah Research Foundation, Salt Lake City, UT (US)

( * ) Notice: Subject to any disclaimer, the term of this patent is extended or adjusted under 35 U.S.C. 154(b) by 818 days.

(21) Appl. No.: 16/148,135

(22) Filed: Oct. 1, 2018

(65) Prior Publication Data

US 2020/0100677 A1 Apr. 2, 2020

(51) Int. Cl.
*A61B 5/01* (2006.01)
*G01R 33/48* (2006.01)
*A61B 5/00* (2006.01)
*A61B 5/055* (2006.01)

(52) U.S. Cl.
CPC .............. *A61B 5/0036* (2018.08); *A61B 5/01* (2013.01); *A61B 5/055* (2013.01); *G01R 33/4804* (2013.01); *A61B 2576/00* (2013.01)

(58) Field of Classification Search
CPC .......... A61B 2576/00; A61B 2576/026; A61B 5/0022; A61B 5/0036; A61B 5/015; A61B 5/055; A61B 2090/374; G01R 33/4804; G01R 33/56563; A61N 7/02
See application file for complete search history.

(56) References Cited

U.S. PATENT DOCUMENTS

| 6,977,502 | B1 * | 12/2005 | Hertz | G01R 33/3621 |
| | | | | 324/318 |
| 8,311,609 | B2 * | 11/2012 | Harvey | G01R 33/4804 |
| | | | | 600/412 |
| 9,748,967 | B1 * | 8/2017 | Serebryanskiy | H03M 1/0634 |
| 10,444,315 | B2 * | 10/2019 | Beck | G01R 33/5676 |
| 2007/0244386 | A1 * | 10/2007 | Steckner | A61B 34/20 |
| | | | | 600/411 |
| 2012/0082357 | A1 * | 4/2012 | Kidane | G01R 33/56518 |
| | | | | 382/131 |

(Continued)

*Primary Examiner* — Baisakhi Roy

(57) ABSTRACT

A method, system and article of manufacture is disclosed. The method includes providing a spatial navigator outside of a thermal therapy region; receiving a plurality of analog-to-digital conversion (ADC) readouts from an MRI device at a plurality of time points, wherein the ADC readouts comprise a first ADC readout acquired at a first time point, and one or more additional ADC readouts acquired at subsequent time points; processing the ADC readouts to obtain a frequency of the spatial navigator at each of the time points; obtaining a main magnetic field ($B_0$) drift of the MRI device based on the frequency of the spatial navigator at a particular time point and the frequency of the spatial navigator at the first time point; and obtaining the temperature change at the particular time point based on the $B_0$ drift.

15 Claims, 7 Drawing Sheets

(56) References Cited

U.S. PATENT DOCUMENTS

2016/0273970 A1* 9/2016 Alon .................... G01K 11/006
2016/0327626 A1* 11/2016 Ha ......................... G01R 33/58
2017/0000376 A1* 1/2017 Partan ................ G01R 33/4814

* cited by examiner

TEMPERATURE MEASUREMENT IN THERMAL THERAPY

TECHNOLOGY FIELD

The present invention relates generally to methods, systems, and apparatuses for measuring a temperature change in a thermal therapy guided by Magnetic Resonance Imaging (MRI) techniques.

BACKGROUND

Thermal therapy is generally guided by Magnetic Resonance Imaging (MRI). The thermal therapy includes Laser Interstitial Thermal Therapy (LITT), High Intensity Focused Ultrasound (HIFU), a microwave ablation, a Radio Frequency (RF) ablation, etc.

In thermal therapy, hydrogen bonds normally existing between water molecules effectively pull electrons away from their protons, increasing the resonant frequency. However, as the temperature of the tissue rises, hydrogen bonds in the tissue stretch, bend, and break. Because of this stretching, bending, and breaking of the hydrogen bonds, the electrons shield the protons from the magnetic field, reducing the main magnetic field ($B_0$) experienced by the protons, and thereby decreasing the overall resonant frequency. The temperature rise causes a change in the MR phase images. The proton resonance frequency shift (PRFS) based Magnetic Resonance (MR) thermometry method captures this temperature change by subtracting a phase image before the thermal therapy (also called a "baseline") from a phase image with temperature rise during thermal therapy, and the temperature difference ($\Delta T$) is calculated by Equation 1 below:

$$\Delta T = \frac{\emptyset_{therm} - \emptyset_{base}}{\alpha \gamma B_0 TE} = \frac{\Delta \emptyset}{\alpha \gamma B_0 TE} \quad (1)$$

In Equation 1, $\gamma$ is the gyromagnetic ratio, TE is echo time, $\emptyset_{therms}$ and $\emptyset_{base}$ are a phase during a thermal therapy, and a phase at a baseline, respectively. However, $B_0$ may be subject to a $B_0$ shift ($\Delta B_0$), and thus the measured temperature may be inaccurate, because the measured temperature often carries contributions from the $B_0$ drift. Thus, there is a need to monitor and obtain the $B_0$ drift during the thermal therapy, so that the temperature change can be calculated accurately in terms of the obtained $B_0$ drift.

SUMMARY

Embodiments of the present disclosure address and overcome one or more of the above shortcomings and drawbacks, by providing methods, systems, and apparatuses which monitors $B_0$ drift during a thermal therapy by placing a dedicated spatial navigator outside of an imaging/therapy region.

In an embodiment, a computer-implemented method of measuring a temperature change during a magnetic resonance imaging (MRI) guided thermal therapy, the method including: providing a spatial navigator outside of a thermal therapy region; receiving a plurality of analog-to-digital conversion (ADC) readouts from an MRI device at a plurality of time points, wherein the ADC readouts comprise a first ADC readout acquired at a first time point, and one or more additional ADC readouts acquired at subsequent time points; processing the ADC readouts to obtain a frequency of the spatial navigator at each of the time points; obtaining a main magnetic field ($B_0$) drift of the MRI device based on the frequency of the spatial navigator at a particular time point and the frequency of the spatial navigator at the first time point; and obtaining the temperature change at the particular time point based on the $B_0$ drift.

In an embodiment, wherein the spatial navigator is one of a crossed-pair navigator and a radio frequency (RF) pencil-beam navigator.

In an embodiment, the method further including: tagging each ADC readout with an indicator prior to processing each ADC readout to obtain the frequency of the spatial navigator; and automatically identifying each ADC readout in an image reconstruction process based on the indicator. The first ADC readout included in the ADC readouts is identified during the image reconstruction process.

In an embodiment, wherein the indicator is one of RTFEEDBACK flag and ONLINE flag.

In an embodiment, the step of processing ADC readouts further including: processing the ADC readouts using inverse Fourier transformation; and averaging transformed ADC readouts to obtain the frequency of the navigator.

In an embodiment, the method further including: interleaving the spatial navigator with acquisition of image data.

In an embodiment, the step of obtaining a $B_0$ drift further including: obtaining a phase drift by subtracting a phase of the first ADC readout from a phase of ADC readout at a particular time point; and obtaining the $B_0$ drift based on the phase drift.

In an embodiment, wherein the spatial navigator is placed on one of a fatty tissue and a non-protein sample.

In an embodiment, a system for measuring a temperature change during a magnetic resonance imaging (MRI) guided thermal therapy, the system including: a magnetic resonance imaging (MRI) device for monitoring the thermal therapy; and a computer system configured to: provide a spatial navigator outside of a thermal therapy region; receive a plurality of analog-to-digital conversion (ADC) readouts from an MRI device at a plurality of time points, wherein the ADC readouts comprise a first ADC readout acquired at a first time point, and one or more additional ADC readouts acquired at subsequent time points; process the ADC readouts to obtain a frequency of the spatial navigator at each of the time points; obtain a main magnetic field ($B_0$) drift of the MRI device based on the frequency of the spatial navigator at a particular time point and the frequency of the spatial navigator at the first time point; and obtain the temperature change at the particular time point based on the $B_0$ drift.

In an embodiment, wherein the spatial navigator is one of a crossed-pair navigator and a radio frequency (RF) pencil-beam navigator.

In an embodiment, the computer system is further configured to: tag each ADC readout with an indicator prior to processing each ADC readout to obtain the frequency of the spatial navigator; and automatically identify each ADC readout in an image reconstruction process based on the indicator. The first ADC readout included in the ADC readouts is identified during the image reconstruction process.

In an embodiment, wherein the indicator combined with the each ADC readout is one of RTFEEDBACK flag and ONLINE flag.

In an embodiment, the computer system is further configured to: process the ADC readouts using inverse Fourier transformation; and average transformed ADC readouts to obtain the frequency of the navigator.

In an embodiment, the computer system is further configured to: interleave the spatial navigator with acquisition of image data.

In an embodiment, the computer system is further configured to: obtain a phase drift by subtracting a phase of the first ADC readout from a phase of ADC readout at a particular time point; and obtain the $B_0$ drift based on the phase drift.

In an embodiment, wherein the spatial navigator is placed on one of a fatty tissue and a non-protein sample.

In an embodiment, an article of manufacture for measuring a main magnetic field ($B_0$) drift during magnetic resonance imaging (MRI) guided thermal therapy, the article of manufacture comprising a non-transitory, tangible computer-readable medium holding computer-executable instructions for performing a method including: providing a spatial navigator outside of a thermal therapy region; receiving a plurality of one analog-to-digital conversion (ADC) readouts from an MRI device at a plurality of time points, wherein the ADC readouts comprise a first ADC readout acquired at a first time point and one or more additional readouts acquired at subsequent time points; processing the ADC readouts to obtain a frequency of the spatial navigator at each of the time points; and obtaining a main magnetic field ($B_0$) drift of the MRI device based on the frequency of the spatial navigator at a particular time point and the frequency of the spatial navigator at the first time point.

In an embodiment, the method further including: tagging each ADC readout with an indicator prior to processing each ADC readout to obtain the frequency of the spatial navigator; and automatically identifying each ADC readout in an image reconstruction process based on the indicator. The first readout included in the received readouts is identified during the image reconstruction process.

In an embodiment, the step of processing the ADC readouts further including: processing the ADC readouts using inverse Fourier transformation; and averaging transformed ADC readouts to obtain the frequency of the navigator.

In an embodiment, the step of obtaining a $B_0$ drift further comprising: obtaining a phase drift by subtracting a phase of the first ADC readout from a phase of ADC readout at a particular time point; and obtaining the $B_0$ drift based on the phase drift.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes several embodiments directed at methods, systems, and apparatuses related to MRI temperature imaging. More particularly, the methods, systems, and apparatuses monitor a $B_0$ drift during a thermal therapy, through a dedicated spatial navigator applied outside of an imaging/therapy region (i.e., a region of interest) on a patient. The spatial navigator is separate from the imaging/therapy region, and thus the temperature change in the imaging/therapy region would not impact on the measurement of $B_0$ drift. Meanwhile, $B_0$ drift measurement would also not impact on the imaging/therapy region due to the separate and dedicated spatial navigator (i.e., 2D spatially selective RF pulses).

According to various embodiments of the present invention, described in more detail below, thermal therapy is implemented through an ablation device, for example, a LITT device, a HIFU device, a microwave ablation device, or a RF ablation device. During the thermal treatment, a patient is placed in a MRI Scanner, which is used to locate a targeted tissue to be ablated, monitor a temperature change using MRI thermometry data, and produce detailed images of the targeted tissue, so that the physician can observe the treatment situation in real time.

Figure 1:
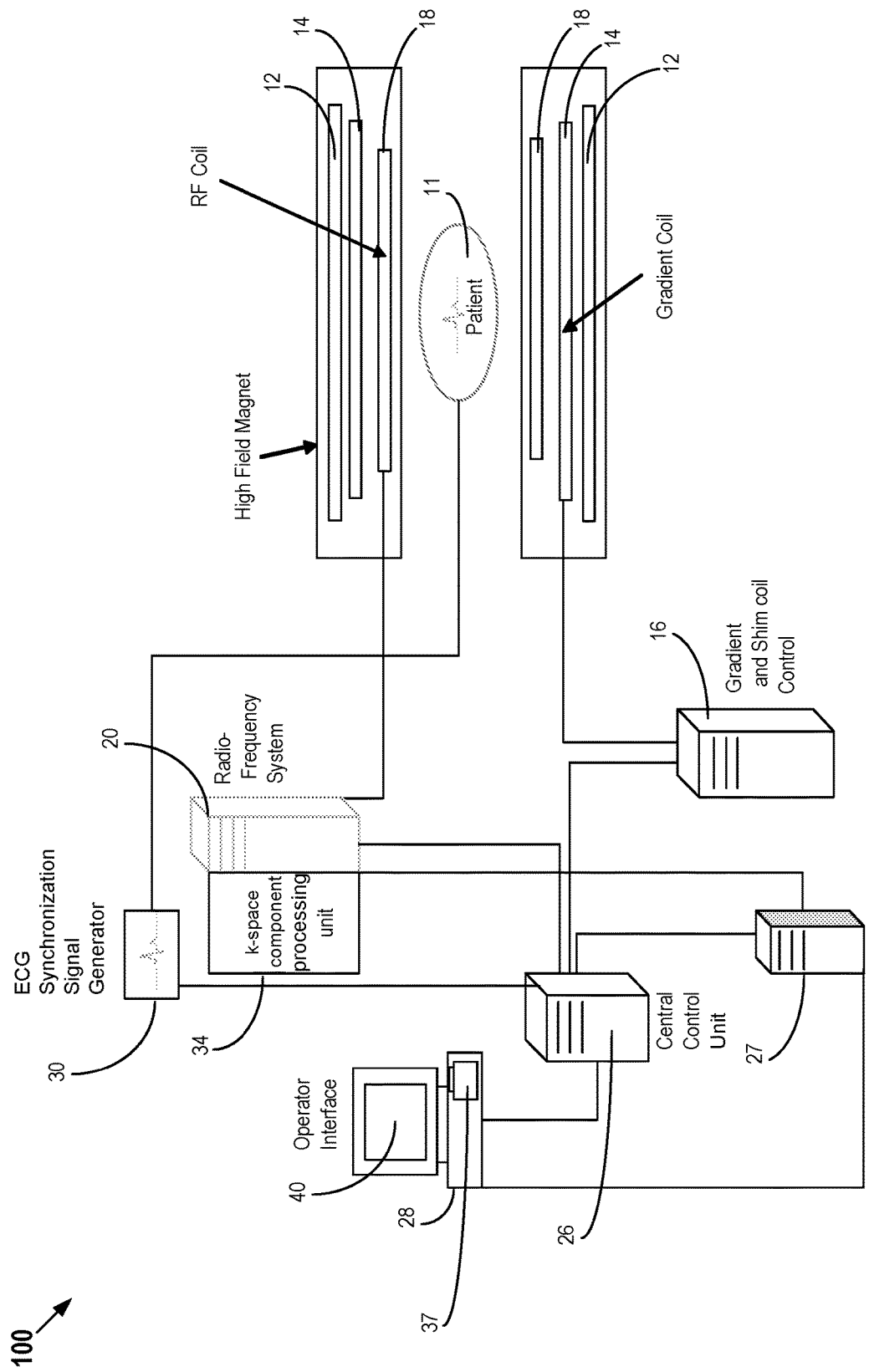
FIG. 1 shows a system for a MRI scanner, as used by some embodiments described herein.

FIG. 1 shows a MRI Scanner, i.e., a system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further, radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processing unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processing unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of a magnetic resonance dataset representing a magnetic resonance image. A storage processor in the k-space component processing unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components are substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on operator interface 40 of a display. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on operator interface 40, for example. Various techniques may be used for reconstruction.

Figure 2:
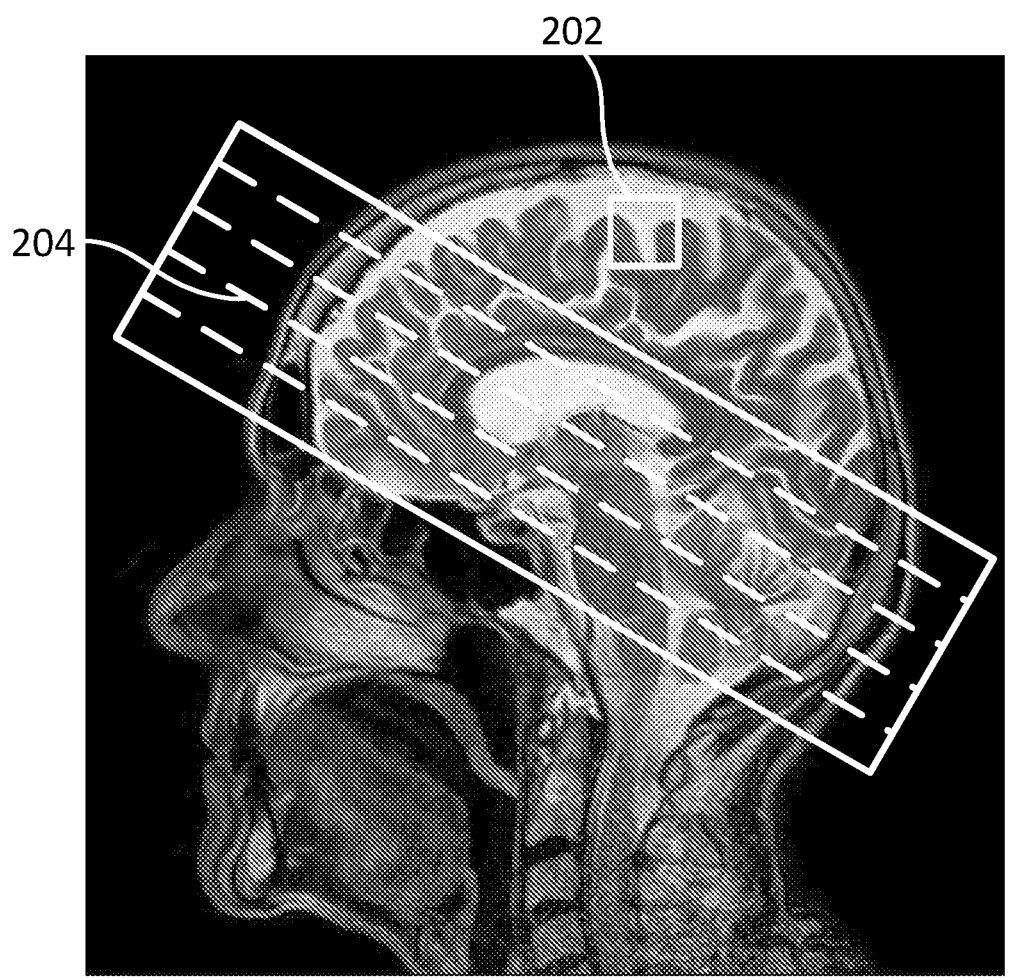
FIG. 2 illustrates placement of a $B_0$ drift navigator with respect to an imaging/therapy region of a human brain, according to some embodiments described herein.

FIG. 2 illustrates placement of a navigator with respect to an imaging/therapy region of a human brain. As shown in FIG. 2, a navigator 202 is placed outside of imaging region (i.e., therapy region) 204. In some embodiments, this navigator is a dedicated 2D spatial navigator, for example, using 2D spatially selective RF pulses. By placing the navigator 202 outside of the imaging region 204, the temperature change in the imaging region 204 would have no impact on the navigator 202. Furthermore, the navigator 202 is provided merely for $B_0$ drift monitoring, and thus the imaging region 204 will not be affected by the navigator 202.

Figure 3:
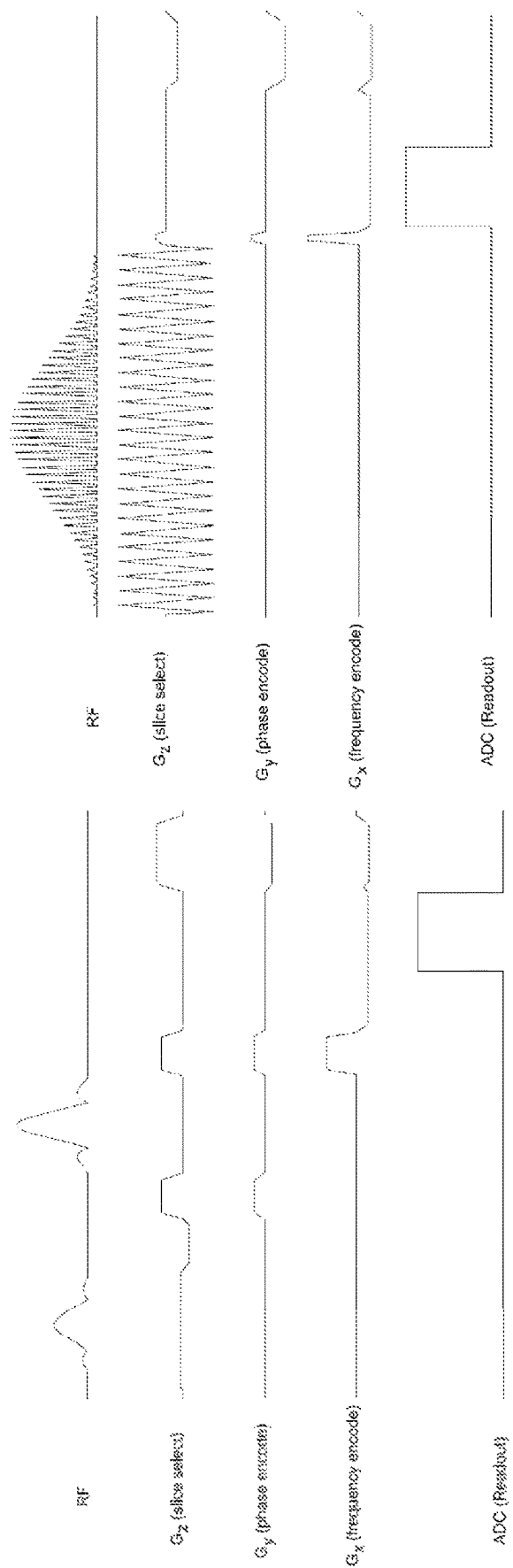
FIG. 3A illustrates a sequence diagram of applying a crossed-pair navigator, according to some embodiments described herein.
FIG. 3B illustrates a sequence diagram of applying a pencil-beam navigator, according to some embodiments described herein.

In an embodiment, the navigator 202 can be a crossed-pair navigator, or 2D RF pencil-beam navigator, as shown in FIG. 3A and FIG. 3B, respectively. A single analog-to-digital conversion (ADC) readout (i.e., digital signal converted from a magnetic resonance signal received by the RF coil 18 when performing frequency encoding), as shown in the respective last row of FIG. 3A and FIG. 3B, is generated when applying either the crossed-pair navigator or the pencil-beam navigator. In an embodiment, each single ADC readout, which is generated when applying the navigator 202 each time, can be tagged with a flag, so that all the ADC readouts can be identified later in an image reconstruction pipeline. The first navigator, corresponding to the first single readout, will act as a reference (baseline) for calculating a phase shift and a $B_0$ drift.

In some embodiments, each ADC readout is tagged with an indicator, e.g., a flag (i.e., an on/off switch), when the ADC readout is generated from the magnetic resonance signal received by the RF coil 18 (see FIG. 1). For example, if the operator enables "$B_0$ drift monitor" function through the operator interface 40 (see FIG. 1), then the indicator, e.g. a special flag RTFEEDBACK (real time feedback), is turned on, and each ADC readout is automatically tagged with an indicator. On the contrary, if the operator disables "$B_0$ drift monitor" function through the operator interface 40, then the indicator, e.g. RTFEEDBACK is turned off, and no indicator will be tagged with ADC readouts. The special flag RTFEEDBACK can be used to identify each ADC readout, for example, when reconstructing images. The identified ADC readouts result from applying the navigator 202 dedicated for monitoring $B_0$ drift, and thus the identified ADC readouts can be used to calculate the $B_0$ drift. In another embodiment, each ADC readout can be tagged with a flag other than RTFEEDBACK, as long as the ADC readouts can be identified during the reconstruction process. Each ADC readout, generated in response to applying navigator 202, is tagged with a flag or indicator, so that the tagged ADC readout can be easily identified in the later image reconstruction process.

After the ADC readouts are identified, an inverse Fourier transform is performed on the ADC readouts. The transformed readouts can then be averaged to calculate the frequency $f_k$ of the navigator 202 through Equation 2 below, where $F_n$ is the transformed inverse Fourier data, and N is the number of samples:

$$f_k = \frac{1}{N} \sum_{n=0}^{N-1} F_n e^{-2\pi i k n / N} \qquad (2)$$

A phase drift $\Delta\varnothing_{t_p}$ is then calculated through Equation 3 below, $$\Delta\emptyset_{t_p} = \frac{1}{N}\sum_{k=0}^{N-1} \text{angle}\left(f_{k_{t_p}} f^*_{k_{t_0}}\right) \text{ or } \Delta\emptyset_{t_p} = \text{angle}\left(\frac{1}{N}\sum_{k=0}^{N-1} f_{k_{t_p}} f^*_{k_{t_0}}\right) \quad (3)$$

In the Equation 3, $$f_{k_{t_p}}$$

is a frequency of the navigator 202 at a time point $t_p$ (corresponding to a navigator other than the first navigator), $$f^*_{k_{t_0}}$$

is a convolution of the frequency of the navigator 202 at a time point $t_0$ (corresponding to the first navigator), and angle ($f_{k_{t_p}} f^*_{k_{t_0}}$) is an angle (phase) of complex conjugate multiplication between $$f_{k_{t_p}} \text{ and } f_{k_{t_0}}.$$

Alternatively, complex conjugate multiplication of $$f_{k_{t_p}} \text{ and } f_{k_{t_0}}$$

can be averaged first and then the angle (phase) of the average complex value is obtained, which avoids accumulating wrap around errors when the average is near pi ($\pi$). The first navigator (corresponding to the time point $t_0$) acts as a reference, whose phase can be subtracted from the phase of the navigator at the time point $t_p$, so that the phase difference $\Delta\emptyset_{t_p}$ can be calculated to effectively measure the phase "drift" from the first phase value (corresponding to the first navigator). The complex conjugate multiplication in Equation (3) signifies subtraction in the complex domain.

As noted above, the navigator 202 is placed outside of the imaging region/therapy region, and thus is not affected by the temperature change. Because the phase drift $\Delta\emptyset_{t_p}$ is calculated through a navigator 202 unaffected by the temperature change, the $B_0$ drift $\Delta B_0$ is equivalent to the phase drift $\Delta\emptyset_{t_p}$. The $B_0$ drift can then be substituted into Equation 1 to accurately calculate the temperature difference (i.e., temperature change).

Figure 4:
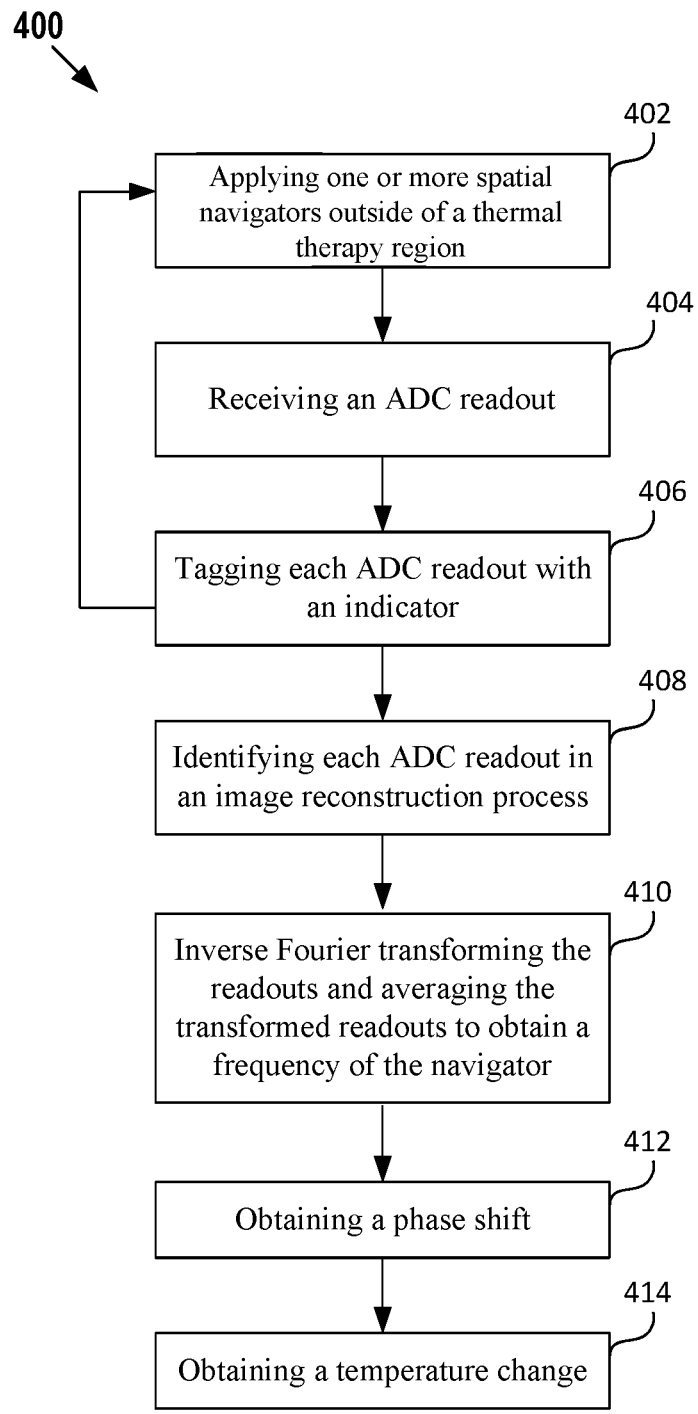
FIG. 4 illustrates a flowchart of a method of measuring a temperature change during a thermal therapy, according to some embodiments described herein.

FIG. 4 illustrates a flowchart of a method 400 of measuring a temperature change during a thermal therapy, according to some embodiments described herein. At step 402, one or more spatial navigators are applied outside of the region where thermal therapy will be performed (referred to herein as the "thermal therapy region"). The spatial navigator is applied specifically for monitoring the $B_0$ drift, and can be, for example, a crossed-pair navigator, or a 2D RF pencil-beam navigator. Application of the spatial navigator is interleaved with the imaging volume acquisition, and the frequency of interleaving is decided by a user (e.g., an operator or a physician). At step 404, a single ADC readout is generated from the analog magnetic resonance signal received from the RF coil 18. At step 406, the ADC readout (i.e., spatial navigator readout) is tagged with a flag (i.e., on/off switch) after applying the spatial navigator. The ADC readout can be tagged with any flag (e.g., RTFEEDBACK, ONLINE, etc.). The ADC readout can be tagged with one flag, or a combination of different flags. The one or more flags are attached to each ADC readout as a data header. Steps 402-406 can be repeated a predetermined number of times (e.g., specified by an operator) to tag a plurality of ADC readouts corresponding to the same number of applied spatial navigators.

Continuing with reference to FIG. 4, at step 408, during an image reconstruction process, all the tagged readouts are identified. Image reconstruction techniques are generally known by those skilled in the art and, in principle, any image reconstruction technique known in the art may be applied at step 408. Next, at step 410, all the tagged ADC readouts are processed using an inverse Fourier transformation, and the transformed ADC readouts are averaged to obtain a frequency of the navigator through Equation 2. At step 412, a phase shift (equivalent to the $B_0$ drift) is calculated through Equation 3. Then, at step 414, this phase shift is used to calculate a temperature change in the thermal therapy region through Equation 1.

Figure 5:
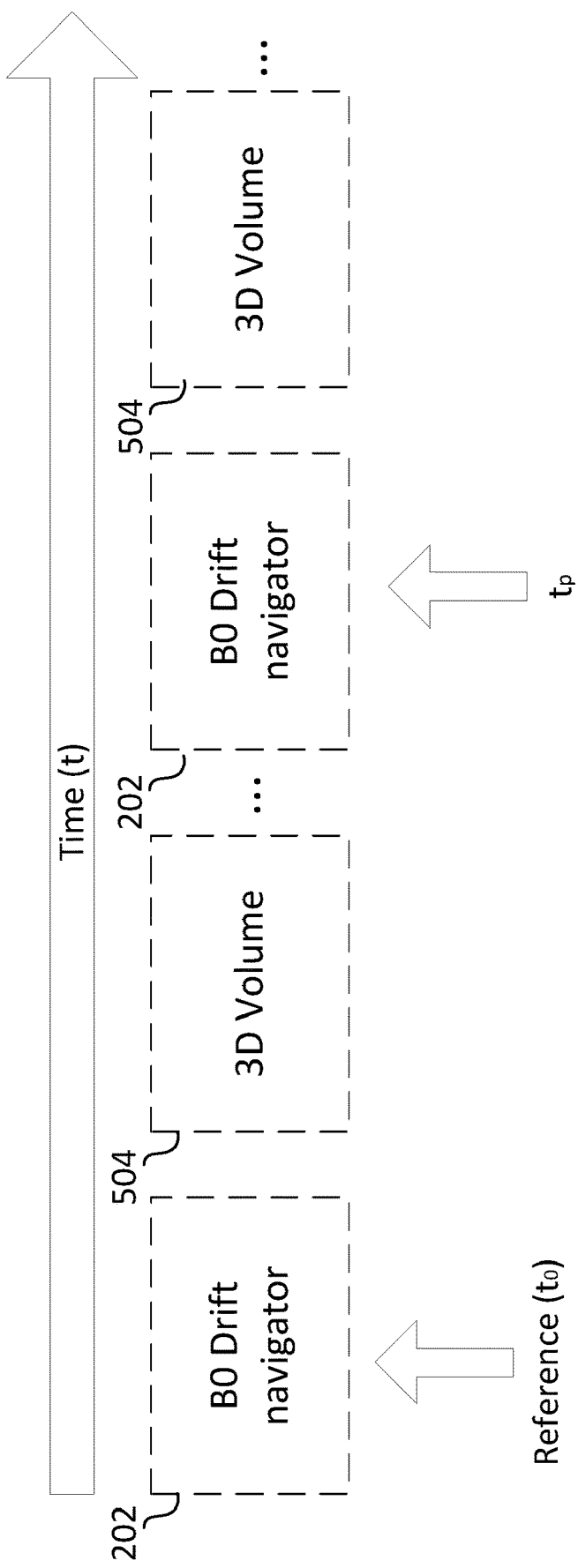
FIG. 5 illustrates an acquisition strategy of the $B_0$ drift navigator, according to some embodiments described herein.
Figure 6:
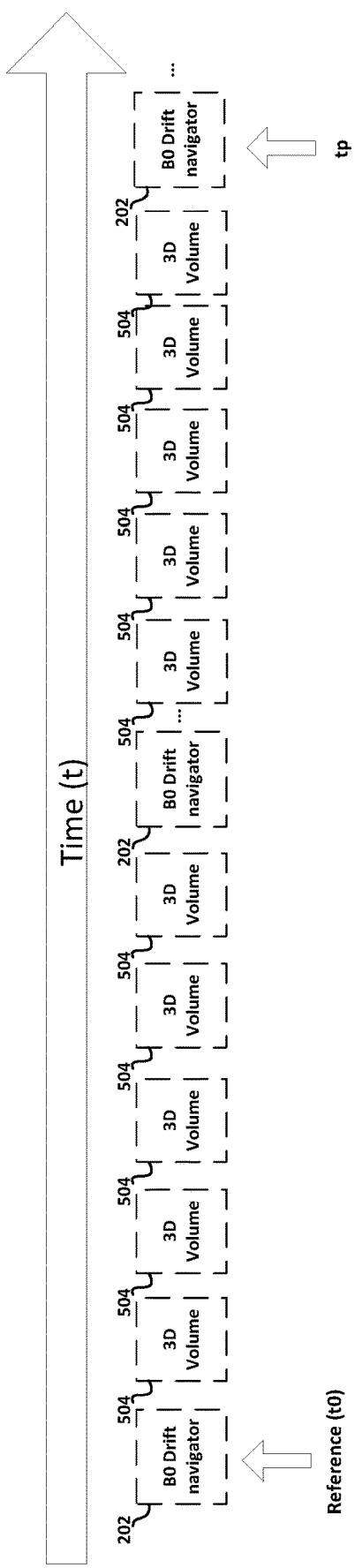
FIG. 6 illustrates another acquisition strategy of the $B_0$ drift navigator, according to some embodiments described herein.

FIG. 5 and FIG. 6 illustrate acquisition strategies of the $B_0$ drift navigator 202. As shown in FIG. 5 and FIG. 6, application of the $B_0$ drift navigator 202 could be interleaved with imaging acquisitions. The frequency of interleaving could be set through a user input. In an embodiment, as shown in FIG. 5, application of $B_0$ drift navigator 202 is interleaved with one 3D imaging volume 504, i.e., the $B_0$ drift navigator 202 is applied after every imaging acquisition. In another embodiment, as shown in FIG. 6, application of $B_0$ drift navigator 202 is interleaved with five 3D imaging volumes 504, i.e., the $B_0$ drift navigator 202 is applied after every five imaging acquisitions.

In an embodiment, the $B_0$ drift navigator 202 can be placed on fatty tissues. In another embodiment, the $B_0$ drift navigator 202 can be placed on non-protein samples. For example, a fluorine bottle or oil bottle can be attached to the patient's body, and the $B_0$ drift navigator 202 is placed on the fluorine bottle or oil bottle. The Larmor frequency of fatty tissues, or non-protein samples is different from the Larmor frequency of water, which is the major constituent of the human body, and thus it's easy to independently "excite" (using RF transmission) and "receive" (at the excitation frequency) $B_0$ drift data and normal imaging acquisition data.

In an embodiment, the calculated $B_0$ drift can be used to adjust transmit excitation frequency (i.e., RF excitation frequency). While adjusting the transmit excitation frequency, the radiofrequency field ($B_1$) is adjusted to account for the change in resonance caused by $B_0$, and the transmit excitation frequency is directly proportional to $B_0$. Thus, referring to Equation 1, the temperature change is captured taking into account $B_0$ drift.

Figure 7:
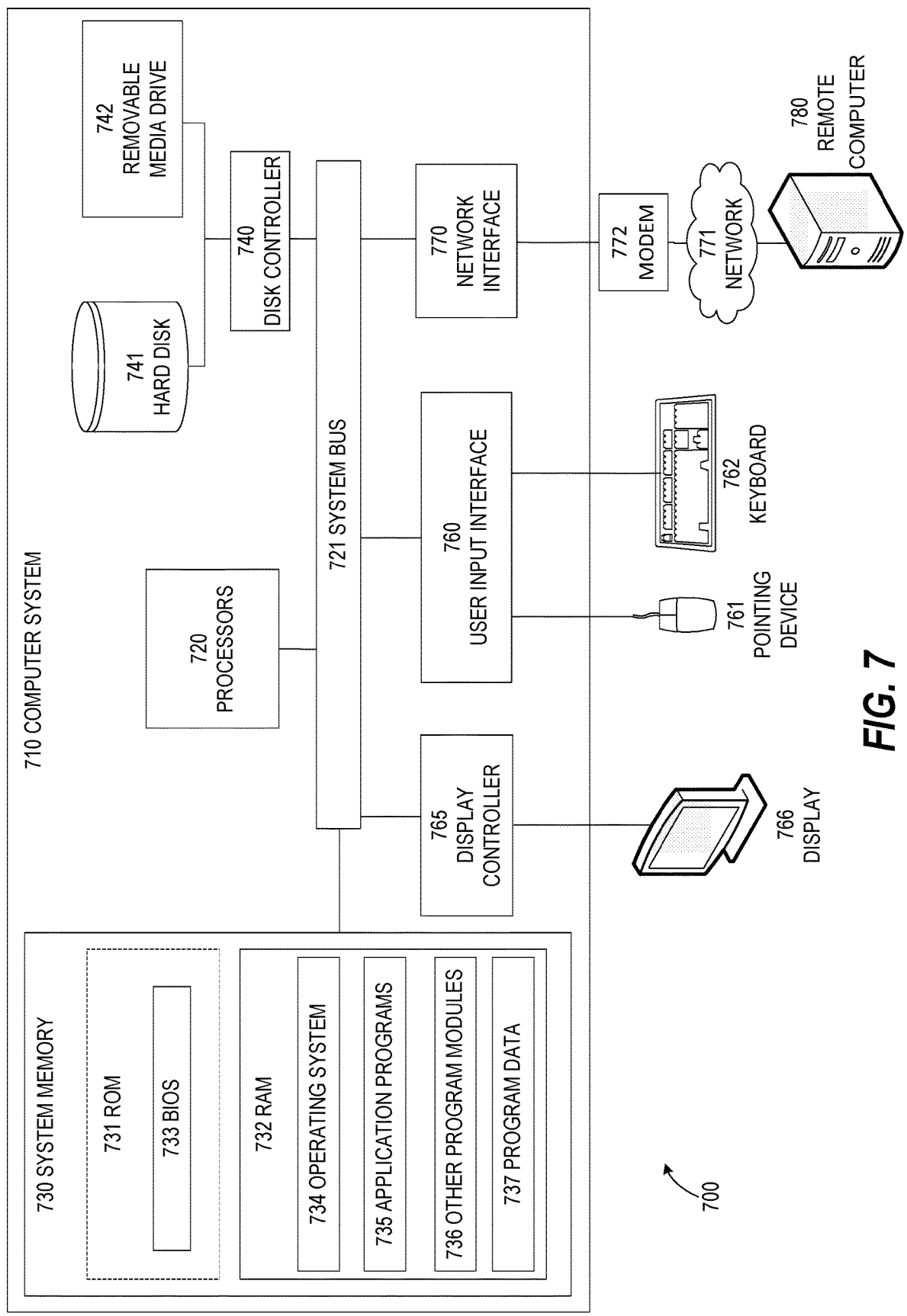
FIG. 7 illustrates an exemplary computing environment within which embodiments of the invention may be implemented.

FIG. 7 illustrates an exemplary computing environment 700 within which embodiments of the invention may be implemented. For example, this computing environment 700 may be used to implement the temperature change measurement process 400, described in FIG. 4. In some embodiments, the computing environment 700 may be used to implement one or more of the components illustrated in the system 100 of FIG. 1. The computing environment 700 may include computer system 710, which is one example of a computing system upon which embodiments of the invention may be implemented. Computers and computing environments, such as computer system 710 and computing environment 700, are known to those of skill in the art and thus are described briefly here.

As shown in FIG. 7, the computer system 710 may include a communication mechanism such as a system bus 721 or other communication mechanism for communicating information within the computer system 710. The computer system 710 further includes one or more processors 720 coupled with the system bus 721 for processing the information. The processors 720 may include one or more central processing units (CPUs), graphical processing units (GPUs), or any other processor known in the art.

The computer system 710 also includes a system memory 730 coupled to the system bus 721 for storing information and instructions to be executed by processors 720. The system memory 730 may include computer readable storage media in the form of volatile and/or nonvolatile memory, such as read only memory (ROM) 731 and/or random access memory (RAM) 732. The system memory RAM 732 may include other dynamic storage device(s) (e.g., dynamic RAM, static RAM, and synchronous DRAM). The system memory ROM 731 may include other static storage device(s) (e.g., programmable ROM, erasable PROM, and electrically erasable PROM). In addition, the system memory 730 may be used for storing temporary variables or other intermediate information during the execution of instructions by the processors 720. A basic input/output system (BIOS) 733 containing the basic routines that help to transfer information between elements within computer system 710, such as during start-up, may be stored in ROM 731. RAM 732 may contain data and/or program modules that are immediately accessible to and/or presently being operated on by the processors 720. System memory 730 may additionally include, for example, operating system 734, application programs 735, other program modules 736 and program data 737.

The computer system 710 also includes a disk controller 740 coupled to the system bus 721 to control one or more storage devices for storing information and instructions, such as a hard disk 741 and a removable media drive 742 (e.g., floppy disk drive, compact disc drive, tape drive, and/or solid state drive). The storage devices may be added to the computer system 710 using an appropriate device interface (e.g., a small computer system interface (SCSI), integrated device electronics (IDE), Universal Serial Bus (USB), or FireWire).

The computer system 710 may also include a display controller 765 coupled to the system bus 721 to control a display 766, such as a cathode ray tube (CRT) or liquid crystal display (LCD), for displaying information to a computer user. The computer system includes a user input interface 760 and one or more input devices, such as a keyboard 762 and a pointing device 761, for interacting with a computer user and providing information to the processors 720. The pointing device 761, for example, may be a mouse, a trackball, or a pointing stick for communicating direction information and command selections to the processor 720 and for controlling cursor movement on the display 766. The display 766 may provide a touch screen interface which allows input to supplement or replace the communication of direction information and command selections by the pointing device 761.

The computer system 710 may perform a portion of or all of the processing steps of embodiments of the invention in response to the processors 720 executing one or more sequences of one or more instructions contained in a memory, such as the system memory 730. Such instructions may be read into the system memory 730 from another computer readable medium, such as a hard disk 741 or a removable media drive 742. The hard disk 741 may contain one or more datastores and data files used by embodiments of the present invention. Datastore contents and data files may be encrypted to improve security. The processors 720 may also be employed in a multi-processing arrangement to execute the one or more sequences of instructions contained in system memory 730. In alternative embodiments, hard-wired circuitry may be used in place of or in combination with software instructions. Thus, embodiments are not limited to any specific combination of hardware circuitry and software.

As stated above, the computer system 710 may include at least one computer readable medium or memory for holding instructions programmed according to embodiments of the invention and for containing data structures, tables, records, or other data described herein. The term "computer readable medium" as used herein refers to any medium that participates in providing instructions to the processors 720 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 741 or removable media drive 742. Non-limiting examples of volatile media include dynamic memory, such as system memory 730. Non-limiting examples of transmission media include coaxial cables, copper wire, and fiber optics, including the wires that make up the system bus 721. Transmission media may also take the form of acoustic or light waves, such as those generated during radio wave and infrared data communications.

The computing environment 700 may further include the computer system 710 operating in a networked environment using logical connections to one or more remote computers, such as remote computer 780. Remote computer 780 may be a personal computer (laptop or desktop), a mobile device, a server, a router, a network PC, a peer device or other common network node, and typically includes many or all of the elements described above relative to computer system 710. When used in a networking environment, computer system 710 may include modem 772 for establishing communications over a network 771, such as the Internet. Modem 772 may be connected to system bus 721 via user network interface 770, or via another appropriate mechanism.

Network 771 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 710 and other computers (e.g., remote computer 780). The network 771 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 771.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. § 112 (f), unless the element is expressly recited using the phrase "means for."

We claim:

1. A computer-implemented method of measuring a temperature change during a magnetic resonance imaging (MRI) guided thermal therapy, the method comprising:
providing a spatial navigator applied outside of a thermal therapy region of interest on a patient;
receiving a plurality of analog-to-digital conversion (ADC) readouts from an MM device at a plurality of time points, wherein the ADC readouts comprise a first ADC readout acquired at a first time point, and one or more additional ADC readouts acquired at subsequent time points;
processing the ADC readouts to obtain a frequency of the spatial navigator at each of the time points;
obtaining a main magnetic field ($B_0$) drift of the MRI device based on the frequency of the spatial navigator at a particular time point and the frequency of the spatial navigator at the first time point;
obtaining the temperature change at the particular time point based on the $B_0$ drift;
tagging each ADC readout with an indicator prior to processing each ADC readout to obtain the frequency of the spatial navigator, wherein the indicator indicates that a function of monitoring the main magnetic field drift is enabled, wherein the indicator is one of RTFEEDBACK flag and ONLINE flag; and
automatically identifying each ADC readout in an image reconstruction process based on the indicator,
wherein the first ADC readout included in the ADC readouts is identified during the image reconstruction process.

2. The method of claim 1, wherein the spatial navigator is one of a crossed-pair navigator and a radio frequency (RF) pencil-beam navigator.

3. The method of claim 1, the step of processing ADC readouts further comprising:
processing the ADC readouts using inverse Fourier transformation; and
averaging transformed ADC readouts to obtain the frequency of the navigator.

4. The method of claim 3, further comprising:
interleaving the spatial navigator with acquisition of image data.

5. The method of claim 3, the step of obtaining a $B_0$ drift further comprising:
obtaining a phase drift by subtracting a phase of the first ADC readout from a phase of ADC readout at a particular time point; and
obtaining the $B_0$ drift based on the phase drift.

6. The method of claim 1, wherein the spatial navigator is placed on one of a fatty tissue and a non-protein sample.

7. A system for measuring a temperature change during a magnetic resonance imaging (MM) guided thermal therapy, the system comprising:
a magnetic resonance imaging (MRI) device for monitoring the thermal therapy; and
a computer system configured to:
provide a spatial navigator applied outside of a thermal therapy region of interest on a patient;
receive a plurality of analog-to-digital conversion (ADC) readouts from an MM device at a plurality of time points, wherein the ADC readouts comprise a first ADC readout acquired at a first time point, and one or more additional ADC readouts acquired at subsequent time points;
process the ADC readouts to obtain a frequency of the spatial navigator at each of the time points;
obtain a main magnetic field ($B_0$) drift of the MRI device based on the frequency of the spatial navigator at a particular time point and the frequency of the spatial navigator at the first time point;

obtain the temperature change at the particular time point based on the $B_0$ drift;

tag each ADC readout with an indicator prior to processing each ADC readout to obtain the frequency of the spatial navigator, wherein the indicator indicates that a function of monitoring the main magnetic field drift is enabled, wherein the indicator is one of RTFEEDBACK flag and ONLINE flag; and automatically identify each ADC readout in an image reconstruction process based on the indicator, wherein the first ADC readout included in the ADC readouts is identified during the image reconstruction process.

8. The system of claim 7, wherein the spatial navigator is one of a crossed-pair navigator and a radio frequency (RF) pencil-beam navigator.

9. The system of claim 7, the computer system is further configured to:

process the ADC readouts using inverse Fourier transformation; and average transformed ADC readouts to obtain the frequency of the navigator.

10. The system of claim 9, the computer system is further configured to:

obtain a phase drift by subtracting a phase of the first ADC readout from a phase of ADC readout at a particular time point; and obtain the $B_0$ drift based on the phase drift.

11. The system of claim 10, wherein the spatial navigator is placed on one of a fatty tissue and a non-protein sample.

12. The system of claim 7, the computer system is further configured to:

interleave the spatial navigator with acquisition of image data.

13. An article of manufacture for measuring a main magnetic field ($B_0$) drift during magnetic resonance imaging (MRI) guided thermal therapy, the article of manufacture comprising a non-transitory, tangible computer-readable medium holding computer-executable instructions for performing a method comprising:

providing a spatial navigator applied outside of a thermal therapy region of interest on a patient;

receiving a plurality of one analog-to-digital conversion (ADC) readouts from an MM device at a plurality of time points, wherein the ADC readouts comprise a first ADC readout acquired at a first time point and one or more additional readouts acquired at subsequent time points;

processing the ADC readouts to obtain a frequency of the spatial navigator at each of the time points;

obtaining a main magnetic field ($B_0$) drift of the MRI device based on the frequency of the spatial navigator at a particular time point and the frequency of the spatial navigator at the first time point;

tagging each ADC readout with an indicator prior to processing each ADC readout to obtain the frequency of the spatial navigator, wherein the indicator indicates that a function of monitoring the main magnetic field drift is enabled, wherein the indicator is one of RTFEEDBACK flag and ONLINE flag; and automatically identifying each ADC readout in an image reconstruction process based on the indicator, wherein the first readout included in the received readouts is identified during the image reconstruction process.

14. The article of manufacture of claim 13, the step of processing the ADC readouts further comprising:

processing the ADC readouts using inverse Fourier transformation; and averaging transformed ADC readouts to obtain the frequency of the navigator.

15. The article of manufacture of claim 13, the step of obtaining a $B_0$ drift further comprising:

obtaining a phase drift by subtracting a phase of the first ADC readout from a phase of ADC readout at a particular time point; and obtaining the $B_0$ drift based on the phase drift.

* * * * *